United States Patent
Wollenberg et al.

(10) Patent No.: US 7,579,192 B2
(45) Date of Patent: *Aug. 25, 2009

(54) HIGH THROUGHPUT SCREENING METHODS FOR LUBRICATING OIL COMPOSITIONS

(75) Inventors: Robert H. Wollenberg, Orinda, CA (US); Thomas J. Balk, San Francisco, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 707 days.

This patent is subject to a terminal disclaimer.

(21) Appl. No.: 10/699,507

(22) Filed: Oct. 31, 2003

(65) Prior Publication Data

US 2005/0095716 A1    May 5, 2005

(51) Int. Cl.
*G01N 33/26* (2006.01)
(52) U.S. Cl. .............. 436/60; 436/43; 436/55; 436/164; 436/174; 422/63; 422/67; 422/82.05; 508/110; 506/7; 506/23; 506/27; 506/33; 506/37; 506/39; 506/40; 702/30
(58) Field of Classification Search .......... 436/60, 436/164, 165, 55, 174, 180, 43; 422/63, 422/67, 68.1, 82.05, 82.09, 61, 62, 100, 102; 435/DIG. 2, DIG. 9, DIG. 22, DIG. 29, DIG. 45; 508/110; 506/7, 33, 37, 39, 40, 23, 27, 43; 702/30
See application file for complete search history.

(56) References Cited

U.S. PATENT DOCUMENTS

| | | | |
|---|---|---|---|
| 5,715,046 A * | 2/1998 | Tolvanen et al. .............. 356/70 |
| 5,959,297 A | 9/1999 | Weinberg et al. | |
| 5,985,356 A | 11/1999 | Shultz et al. | |
| 5,993,662 A * | 11/1999 | Garr et al. .................... 210/656 |
| 6,004,617 A | 12/1999 | Shultz et al. | |
| 6,030,917 A | 2/2000 | Weinberg et al. | |
| 6,034,775 A | 3/2000 | McFarland et al. | |
| 6,045,671 A | 4/2000 | Wu et al. | |
| 6,087,181 A | 7/2000 | Cong | |
| 6,149,882 A | 11/2000 | Guan et al. | |
| 6,157,449 A | 12/2000 | Hajduk | |

(Continued)

FOREIGN PATENT DOCUMENTS

EP    1233361    *   8/2002

(Continued)

OTHER PUBLICATIONS

Hawley, G. The Condensed Chemical Dictionary, tenth edition, 1981, p. 20.*

*Primary Examiner*—Maureen M Wallenhorst
(74) *Attorney, Agent, or Firm*—Claude J. Caroli; M. Carmen & Associates, PLLC (57) ABSTRACT

A method for determining storage stability for a plurality of fluid lubricant samples of different compositions is provided. Each sample includes one or more lubricating oil additives, or a combination of one or more lubricant base oils and one or more lubricating oil additives. The methods can advantageously be optimized using combinatorial chemistry, in which a database of combinations of lubricating oil additives or lubricating oil compositions containing such additives are generated. As market conditions vary and/or product requirements or customer specifications change, conditions suitable for forming desired products can be identified with little or no downtime.

42 Claims, 3 Drawing Sheets

U.S. PATENT DOCUMENTS

| | | | |
|---|---|---|---|
| 6,175,409 | B1 | 1/2001 | Nielsen et al. |
| 6,182,499 | B1 | 2/2001 | McFarland et al. |
| 6,187,164 | B1 | 2/2001 | Warren et al. |
| 6,248,540 | B1 | 6/2001 | Weinberg et al. |
| 6,260,407 | B1 | 7/2001 | Petro et al. |
| 6,265,226 | B1 | 7/2001 | Petro et al. |
| 6,296,771 | B1 | 10/2001 | Miroslav |
| 6,326,090 | B1 | 12/2001 | Shultz et al. |
| 6,336,353 | B2 | 1/2002 | Matsiev et al. |
| 6,345,528 | B2 | 2/2002 | Petro et al. |
| 6,346,290 | B1 | 2/2002 | Schultz et al. |
| 6,371,640 | B1 | 4/2002 | Hajduk et al. |
| 6,373,570 | B1 | 4/2002 | McFarland et al. |
| 6,393,895 | B1 | 5/2002 | Matsiev et al. |
| 6,393,898 | B1 | 5/2002 | Hajduk et al. |
| 6,395,552 | B1 | 5/2002 | Borade et al. |
| 6,401,519 | B1 | 6/2002 | McFarland et al. |
| 6,406,632 | B1 | 6/2002 | Safir et al. |
| 6,410,331 | B1 | 6/2002 | Schultz et al. |
| 6,419,881 | B1 | 7/2002 | Weinberg et al. |
| 6,420,179 | B1 | 7/2002 | Schultz et al. |
| 6,436,292 | B1 | 8/2002 | Petro |
| 6,438,497 | B1 | 8/2002 | Mansky et al. |
| 6,440,745 | B1 | 8/2002 | Weinberg et al. |
| 6,441,901 | B2 | 8/2002 | McFarland et al. |
| 6,461,515 | B1 | 10/2002 | Safir et al. |
| 6,468,806 | B1 | 10/2002 | McFarland et al. |
| 6,475,391 | B2 | 11/2002 | Safir et al. |
| 6,484,567 | B1 | 11/2002 | Hajduk et al. |
| 6,491,816 | B2 | 12/2002 | Petro |
| 6,508,984 | B1 | 1/2003 | Turner et al. |
| 6,519,032 | B1 | 2/2003 | Kuebler et al. |
| 6,528,026 | B2 | 3/2003 | Hajduk et al. |
| 6,535,284 | B1 | 3/2003 | Hajduk et al. |
| 6,535,824 | B1 | 3/2003 | Mansky et al. |
| 6,536,944 | B1 | 3/2003 | Archibald et al. |
| 6,541,271 | B1 | 4/2003 | McFarland et al. |
| 6,553,318 | B2 | 4/2003 | Mansky |
| 6,576,906 | B1 | 6/2003 | Archibald et al. |
| 6,577,392 | B1 | 6/2003 | Nielsen et al. |
| 6,582,116 | B2 | 6/2003 | Nielsen |
| 6,605,473 | B1 | 8/2003 | Hajduk et al. |
| 6,644,101 | B2 | 11/2003 | Hajduk et al. |
| 6,649,413 | B1 | 11/2003 | Schultz et al. |
| 6,650,102 | B2 | 11/2003 | Hajduk et al. |
| 6,653,138 | B1 | 11/2003 | Turner et al. |
| 6,655,194 | B2 | 12/2003 | Hajduk et al. |
| 6,658,429 | B2 | 12/2003 | Dorsett, Jr. |
| 6,664,067 | B1 | 12/2003 | Hajduk et al. |
| 6,668,622 | B2 | 12/2003 | Hajduk et al. |
| 6,670,298 | B1 | 12/2003 | Weinberg et al. |
| 6,679,130 | B2 | 1/2004 | Hajduk et al. |
| 6,681,618 | B2 | 1/2004 | Hajduk et al. |
| 6,686,205 | B1 | 2/2004 | Shultz et al. |
| 6,690,179 | B2 | 2/2004 | Hajduk et al. |
| 2002/0023507 | A1 | 2/2002 | Hajduk et al. |
| 2002/0028456 | A1 | 3/2002 | Manksy et al. |
| 2002/0029621 | A1 | 3/2002 | Hajduk et al. |
| 2002/0032531 | A1 | 3/2002 | Mansy et al. |
| 2002/0098332 | A1 | 7/2002 | Warren et al. |
| 2002/0148282 | A1 | 10/2002 | Hajduk et al. |
| 2002/0155036 | A1 | 10/2002 | Hajduk et al. |
| 2002/0164275 | A1 | 11/2002 | Wheeler et al. |
| 2003/0007152 | A1 | 1/2003 | McFarland et al. |
| 2003/0032198 | A1 | 2/2003 | Lugmair et al. |
| 2003/0032205 | A1 | 2/2003 | McFarland et al. |
| 2003/0037601 | A1 | 2/2003 | Manksy et al. |
| 2003/0037620 | A1 | 2/2003 | Mansky |
| 2003/0041653 | A1 | 3/2003 | Matsiev et al. |
| 2003/0041671 | A1 | 3/2003 | Hajduk et al. |
| 2003/0041672 | A1 | 3/2003 | Hajduk et al. |
| 2003/0041676 | A1 | 3/2003 | Hajduk et al. |
| 2003/0054740 | A1 | 3/2003 | Mansky |
| 2003/0055587 | A1 | 3/2003 | Wang et al. |
| 2003/0056576 | A1 | 3/2003 | Mansky |
| 2003/0068829 | A1 | 4/2003 | Giaquinta et al. |
| 2003/0097871 | A1 | 5/2003 | Mansky |
| 2003/0100119 | A1 | 5/2003 | Weinberg et al. |
| 2003/0100453 | A1 * | 5/2003 | O'Rear ..................... 508/110 |
| 2003/0127776 | A1 | 7/2003 | Carlson et al. |
| 2003/0133113 | A1 | 7/2003 | Hajduk et al. |
| 2003/0138025 | A1 | 7/2003 | Archibald et al. |
| 2003/0141613 | A1 | 7/2003 | Hajduk et al. |
| 2003/0142309 | A1 | 7/2003 | Kuebler et al. |
| 2003/0157721 | A1 | 8/2003 | Turner et al. |
| 2003/0161763 | A1 | 8/2003 | Erden et al. |
| 2003/0169638 | A1 | 9/2003 | Nielsen |
| 2003/0190260 | A1 | 10/2003 | Wheeler et al. |
| 2003/0203500 | A1 | 10/2003 | Carlson et al. |
| 2003/0211016 | A1 | 11/2003 | Dales et al. |
| 2003/0218467 | A1 | 11/2003 | Carlson et al. |
| 2003/0219906 | A1 | 11/2003 | Giaquinta et al. |
| 2004/0123650 | A1 * | 7/2004 | Kolosov et al. ............ 73/54.28 |

FOREIGN PATENT DOCUMENTS

| | | | |
|---|---|---|---|
| WO | 95/13538 | * | 5/1995 |
| WO | 02/07870 | * | 1/2002 |

* cited by examiner

HIGH THROUGHPUT SCREENING METHODS FOR LUBRICATING OIL COMPOSITIONS

BACKGROUND OF THE INVENTION

1. Technical Field

The present invention relates generally to methods for high throughput screening of lubricating oil additives and lubricating oil compositions containing such additives.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the lubricant industry involves individually forming candidate lubricating oil compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading lubricating oil compositions.

Drawbacks associated with conventional screening procedures can be seen as follows. For example, governmental and automotive industry pressure towards reducing the phosphorous and sulfur content of lubricating oil compositions used as, for example, passenger car and heavy duty diesel engine oils, is leading to new research to identify oil compositions which can satisfy certain tests such as, for example, oxidation, wear and compatibility tests, while containing low levels of phosphorous and sulfur. In this context, United States Military Standards MIL-L-46152E and the ILSAC Standards defined by the Japanese and United States Automobile Industry Association at present require the phosphorous content of engine oils to be at or below 0.10 wt. % with future phosphorous content being proposed to even lower levels, e.g., 0.08 wt. % by January, 2004 and below 0.05 wt. % by January, 2006. Also, at present, there is no industry standard requirement for sulfur content in engine oils, but it has been proposed that the sulfur content be below 0.2 wt. % by January, 2006. Thus, it would be desirable to decrease the amount of phosphorous and sulfur in lubricating oils still further, thereby meeting future industry standard proposed phosphorous and sulfur contents in the engine oil while still retaining the oxidation or corrosion inhibiting properties and antiwear properties of the higher phosphorous and sulfur content engine oils. In order to accomplish this, a large number of proposed lubricating oil compositions must be tested to determine which compositions may be useful.

Additionally, similar changes in specifications and changing customer needs also drive reformulation efforts in other lubricant applications such as, for example, transmission fluids, hydraulic fluids, gear oils, marine cylinder oils, compressor oils, refrigeration lubricants and the like.

However, as stated above, present research in the lubricant industry does not allow for reformulation to occur in an expeditious manner. As such, there exists a need in the art for a more efficient, economical and systematic approach for the preparation of lubricating oil compositions and screening of such compositions for information correlating to the actual useful properties of the compositions. For example, many lubricating oil additives, additive concentrates and lubricating oil compositions containing such additives suffer from lack of stability giving rise to sedimentation. This especially occurs during storage under warm temperature or humidity conditions. Thus, in a storage tank containing many thousands of gallons of lubricating oil fluid, a sedimentation rate of a few percent can correspond to a thousand or more gallons of bottom sediment, which is clearly undesirable.

Accordingly, it would be desirable to rapidly screen a plurality of sample candidate lubricating oil additive compositions and lubricating oil compositions containing such lubricating oil additive compositions for storage stability utilizing small amounts of each sample. In this manner, a high throughput preparation and screening of a vast number of diverse compositions can be achieved to identify which lubricating oil additive compositions and lubricating oil compositions containing such lubricating oil additive compositions are compatible and therefore stable.

SUMMARY OF THE INVENTION

A high throughput screening method for determining lubricant performance is provided herein. In accordance with one embodiment of the present invention, a high throughput method for screening lubricating oil additive composition samples, under program control, is provided comprising the steps of (a) providing a plurality of different lubricating oil additive composition samples comprising at least one lubricating oil additive, each sample being in a respective one of a plurality of test receptacles; (b) maintaining each sample at a predetermined temperature and optionally at a predetermined humidity for a predetermined time; (c) measuring the storage stability of each sample to provide storage stability data for each sample; and, (d) outputting the results of step (c).

In another embodiment of the present invention, a system for determining lubricant performance is provided comprising:

a) a plurality of test receptacles, each receptacle containing a different lubricating oil additive composition sample comprising at least one lubricating oil additive;

b) receptacle moving means for individually positioning said test receptacles in a testing station for measurement of storage stability in the respective sample;

c) means for measuring the storage stability in the sample moved to the testing station to obtain storage stability data associated with said sample and for transferring said storage stability data to a computer controller, wherein said computer controller is operatively connected to the means for individually moving the test receptacles.

In yet another embodiment of the present invention, a high throughput method for screening lubricating oil composition samples, under program control, is provided comprising the steps of (a) providing a plurality of different lubricating oil composition samples comprising (i) a major amount of at least one base oil of lubricating viscosity and (ii) a minor amount of at least one lubricating oil additive, each sample being in a respective one of a plurality of test receptacles; (b) maintaining each sample at a predetermined temperature and optionally at a predetermined humidity for a predetermined time; (c) measuring the storage stability of each sample to provide storage stability data for each sample; and, (d) outputting the results of step (c).

BRIEF DESCRIPTION OF THE DRAWINGS

Various embodiments are described below with reference to the drawings wherein.

DETAILED DESCRIPTION OF THE PREFERRED EMBODIMENT(S)

The present invention is directed to a high throughput screening method for determining lubricant performance of lubricating oil additive compositions and lubricating oil compositions containing such lubricating oil additive compositions. The expression "high throughput" as used herein shall be understood to mean that a relatively large number of different lubricating oil additive compositions or lubricating oil compositions can be rapidly prepared and analyzed. In a first step of the screening method of the present invention, at least one lubricating oil additive is introduced in a plurality of respective test receptacles so that each receptacle contains a different lubricating oil additive composition having a different composition depending upon the percentage amounts and/or types of the additives combined in each receptacle.

Alternatively, varying quantities of at least one base oil of lubricating viscosity and at least one lubricating oil additive are introduced in a plurality of respective test reservoirs so that each reservoir contains a different lubricating oil composition having a different composition depending upon the percentage amounts and/or types of the additives combined with the base oil of lubricating viscosity in each receptacle. Data regarding the composition of each sample are stored in a data library. The procedure is advantageously accomplished under program control and automatically controlled by, for example, a microprocessor or other computer control device. The expression "program control" as used herein shall be understood to mean the equipment used herein in providing the plurality of lubricating oil additive compositions or lubricating oil compositions is automated and controlled by a microprocessor or other computer control device.

The lubricating oil additive compositions for use in the high throughput screening method of this invention include at least one lubricating oil additive. Such additives for use herein can be any presently known or later-discovered additive used in formulating lubricating oil compositions. The lubricating oil additives for use herein include, but are not limited to, antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil additive compositions and lubricating oil compositions containing such additives herein.

Alternatively, the lubricating oil additive(s) can further contain a diluent oil to form an additive concentrate. These concentrates usually include at least from about 90 wt. % to about 10 wt. % and preferably from about 90 wt. % to about 50 wt. %, of a diluent oil and from about 10 wt. % to about 90 wt. %, preferably from about 10 wt. % to about 50 wt. %, of the foregoing additive(s). Suitable diluents for the concentrates include any inert diluent, preferably an oil of lubricating viscosity such as, for example, a base oil as described hereinbelow, so that the concentrate may be readily mixed with lubricating oils to prepare lubricating oil compositions. Suitable lubricating oils that may be used as diluents can be any oil of lubricating viscosity.

Examples of antioxidants include, but are not limited to, aminic types, e.g., diphenylamine, phenyl-alpha-napthylamine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; sulfur-containing materials, e.g., sulfurized olefins or esters and the like and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 January 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of detergents include, but are not limited to, overbased or neutral detergents such as sulfonate detergents, e.g., those made from alkyl benzene and fuming sulfuric acid; phenates (high overbased or low overbased), high overbased phenate stearates, phenolates, salicylates, phosphonates, thiophosphonates, ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, thiophosphonamides and phosphoramides; thiazoles, e.g., 2,5-dimercapto-1,3,4-thiadiazoles, mercaptobenzothiazoles and derivatives thereof; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used. Preferably, the dispersants are polyalkylene succinimides derived from animation of polyalkylene succinic anhydrides with polyalkylene polyamine.

The lubricating oil compositions for use in the high throughput screening method of this invention include aminor amount of at least one of the foregoing lubricating oil additives together with a major amount of at least one base oil of lubricating viscosity, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source, or manufacturer's location): that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkyl-methacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

If desired, prior to dispensing the at least one lubricating oil additive or the at least one base oil and at least one lubricating oil additive to provide the compositions herein, as discussed hereinbelow, it can be advantageous to conduct molecular modeling of proposed compounds for use in the compositions (i.e., formulations) to determine which compounds may provide potential leading candidate compositions. For example, calculations can be carried out involving such factors as, for example, transition states, bond-lengths, bond angles, dipole moment, hydrophobicity, etc, of the compounds. This can be carried out using known software such as, for example, Quantum Mechanics available from Accelrys (San Diego, Calif.).

Software for the design of test libraries can be used to design the original compound test libraries based on input from the foregoing experimental program(s). This software can be used to efficiently design test libraries that cover the desired experimental space and utilize statistical experimental design methods. Other software can then be used to analyze the data from the experiments and correlate that data with the structure of the compounds and/or compound treatment conditions and/or reaction conditions. Such correlations are often referred to as QSAR software (Quantitative Structure Activity Relations) available from Accelrys (San Diego, Calif.). Such QSAR programs can then be used by the software to design subsequent compound test libraries for further screening.

The use of such QSAR programs can add to the efficiency of screening. As more data is collected, these QSAR programs can become more efficient at developing compounds libraries with increased probability for finding desirable compounds. For example, the compounds analyzed can be formulated into various lubricating oil compositions, as decribed hereinbelow, and then further analyzed by way of, for example, regression and analysis technologies, using known software, e.g., $C^2$-QSAR available from Accelrys (San Diego, Calif.). In this manner, validation of the data obtained from the molecular modeling can be achieved and then this data can also be stored in a data collector. In this way, new compounds, conceived by one skilled in the art can be checked by the QSAR software to predict their activity prior to their actual synthesis. Additionally, such software tools may be utilized to prioritize a list of possible compounds being considered for synthesis in such a way that one skilled in the art will have a higher probability for success.

Figure 1:
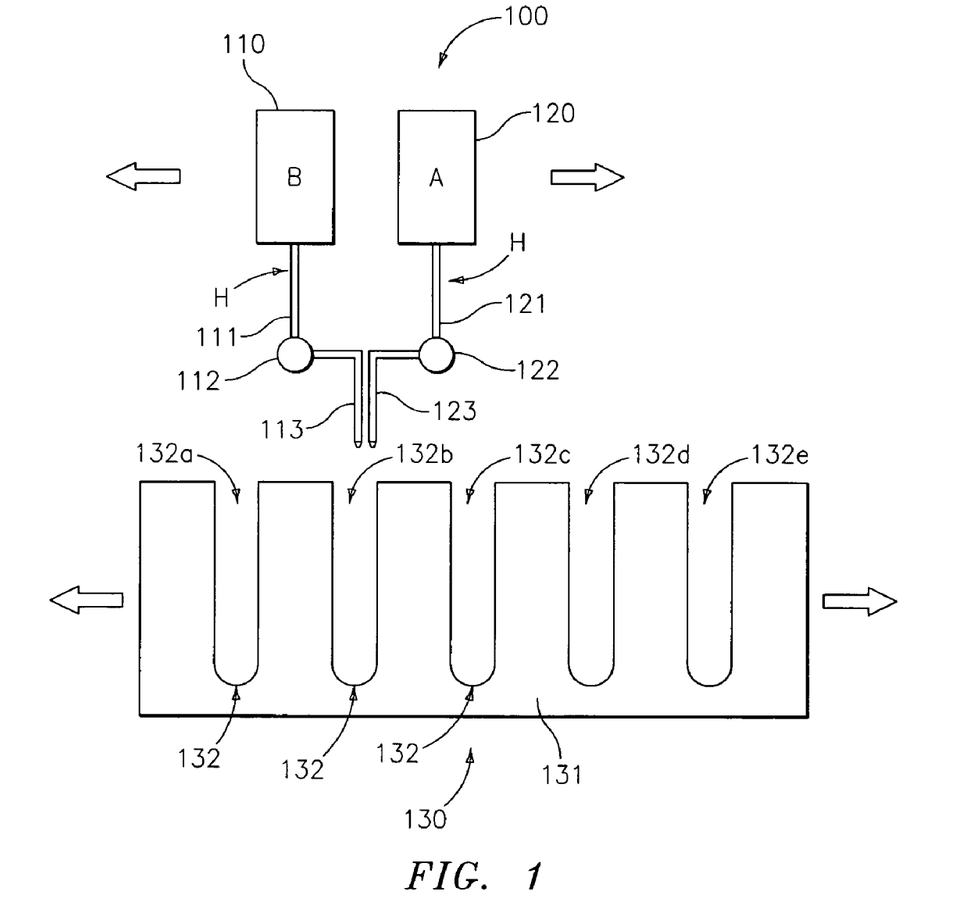
FIG. 1 is a schematic diagram of a system for preparing a plurality of different lubricating oil additive compositions and/or lubricating oil compositions.

Referring now to FIG. 1, an example of a system to provide the foregoing compositions in the plurality of respective test receptacles is generally illustrated as system 100. Representative of this system and method for providing the foregoing compositions in the plurality of respective test receptacles is one disclosed in co-pending U.S. patent application Ser. No. 10/699510filed on Oct. 31, 2003 and entitled "HIGH THROUGHPUT PREPARATION OF LUBRICATING OIL COMPOSITIONS FOR COMBINATORIAL LIBRARIES" by Wollenberg et al. and having a common assignee with the present application, the contents of which are incorporated by reference herein. Generally, vessel 110 contains a supply of the foregoing base oils of lubricating viscosity B. Vessel 120 contains a supply of additive A, which can be any of the foregoing additives useful for modifying the properties of the base oil. As one skilled in the art would readily appreciate, one or more of vessels 110 and vessels 120 can be used when dispensing more than one base oil and/or more than one additive, respectively. For example, in the case of screening lubricating oil additive compositions, one or more vessels 120 can be used without operating vessel 110.

Tubular line 111 is a conduit for communicating the base oil B to nozzle portion 113, from which it can be dispensed into a selected test reservoir, as described below. The amount of base oil dispensed is determined by metering pump 112, which can be computer controlled.

Tubular line 121 is a conduit for communicating the lubricating oil additive A to nozzle portion 123, from which it can be dispensed into a selected test reservoir, as described below. The amount of lubricating oil additive dispensed is determined by metering pump 122, which also can be computer controlled. Computer programs and systems for automatically metering predetermined amounts of materials in accordance with a preselected protocol are known in the art and can be used herein.

Nozzles 113 and 123 are preferably in close proximity so that base oil B and additive A can be simultaneously dispensed in a test reservoir. Alternatively, base oil B and additive A can be sequentially added to the test reservoir. The nozzles 113 and 123 can comprise a multichannel pipette or one or more syringe needles.

The vessels 110 and 120 can be under pressure. Optionally, more than two vessels can be employed. Metering pumps suitable for use in the invention are known and commercially available. In the event that highly viscous lubricant base stock or additives are used, the vessels 110 and 120 and/or the tubular lines 111 and 121, metering pumps 112 and 122, and/or nozzles 113 and 123 can be heated to facilitate fluid flow therethrough.

The test frame 130 includes a block 131 of transparent material (e.g., glass) having a plurality of recesses 132 for receiving the dispensed additives or base oil and additives. The recesses provide test reservoirs wherein each reservoir contains lubricating oil additive compositions or lubricating oil compositions of a different and predetermined composition, i.e., the percentage and/or type of base oil and/or additives in each composition will vary from one reservoir to another. Optionally, the reservoirs can be individual receptacles (e.g., test tubes) mounted upon a rack, instead of being recesses in a block. Preferably, the test receptacles comprise transparent glass tubes. While five reservoirs, i.e., recesses 132*a*, 132*b*, 132*c*, 132*d*, 132*e*, are illustrated in FIG. 1, any number of reservoirs can be employed herein. For example the system can employ 20, 50, 100 or even more test receptacles and samples as required.

The individual reservoirs are adapted to hold relatively small amounts of samples. The sample size in each reservoir can generally be no more than about 20 ml, preferably no more than about 15 ml, more preferably no more than about 10 ml and yet more preferably no more than about 5 ml.

The test frame 130 and dispensing nozzles 113 and 123 are movable relative to one another. Although manual movement of the apparatus by an equipment operator is within the purview of the invention, robotic mechanisms with programmable movement are preferred. In one embodiment the test frame 130 is mounted upon a slidable carriage movable in a lateral and/or vertical direction so as to sequentially position a selected recess under the dispensing nozzles 113 and 123. In another embodiment, the nozzles 113 and 123, and optionally the vessels 110 and 120, are slidably movable laterally and/or vertically to accomplish positioning of the nozzles 113 and 123.

In a testing procedure, vessels 110 and 120 are filled with the selected lubricant base oil and additive(s), respectively. The apparatus of system 100 is moved such that dispensing nozzles 113 and 123 are positioned above and in alignment with recess 132*a*. A metered amount of base oil B and a metered amount of additive A are simultaneously dispensed into recess 132*a*. The dispensing nozzles 113 and 123 are thereafter repositioned to be in alignment with the next recess 132*b* and the metered amounts of additive A and/or base oil B are changed in accordance with a predetermined schedule of variation such that the lubricating oil in recess 132*b* has a different percentage composition of additive than that in recess 132*a*. The pattern is repeated as the nozzles 113 and 123 are sequentially aligned with the successive recesses 132*c*, 132*d*, and 132*e* so that each recess has a predetermined composition of lubricating oil.

The components A and B are preferably combined in the reservoirs by mixing, for example, by agitation of the frame 131, static mixing, individual stirring of the contents of the reservoirs (mechanical or magnetic stirring) and/or by bubbling the reservoir with gas, e.g., nitrogen. Optionally, base oil B and additive(s) A can be combined prior to dispensing into the respective reservoirs. For example, a single dispensing nozzle having a mixing chamber can be used, wherein base oil B and additive(s) A are metered into the mixing chamber and then dispensed through the nozzle into the reservoir.

Figure 2:
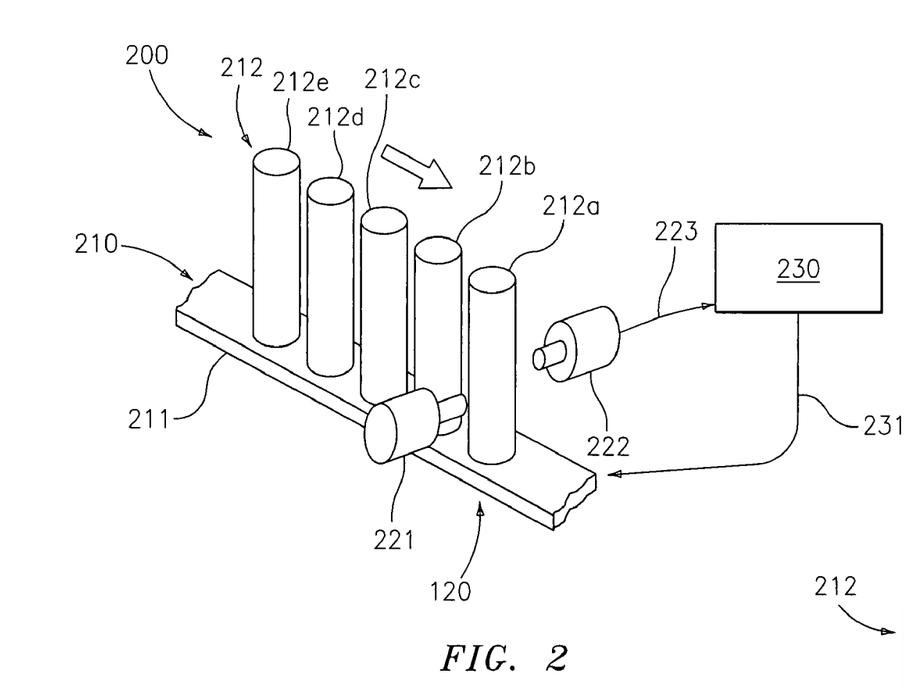
FIG. 2 is a schematic diagram of a system for measuring storage stability of a plurality of samples of different lubricating oil additive compositions and/or lubricating oil compositions.

Once the plurality of receptacles have been provided containing lubricating oil additive compositions and/or lubricating oil compositions, the plurality of fluid samples can then be analyzed for storage stability such as, e.g., sedimentation data, color data, viscosity data, etc. Referring now to FIG. 2, a system for sequentially analyzing a plurality of fluid samples for sedimentation is schematically illustrated. The samples can include lubricating oil additive compositions containing at least one lubricating oil additive or lubricating oil compositions containing one or more base oils and one or more lubricating oil additives, such as those described herein.

System 200 includes means 210 for holding and optionally moving a plurality of test receptacles 212 mounted to a frame 211. In one embodiment a light source 221 is disposed on one side of frame 211 and a photocell 222 is disposed on the opposite side of frame 211 opposite, and aligned with, the light source such that a light beam emitted by the light source 221 can be detected and measured by the photocell 222. In this embodiment, photocell 222 measures the light transmitted through the sample. In another embodiment, photocell 222 is mounted so as to be aligned at a suitable angle, preferably 90°, to the incident light beam from light source 221. In this second embodiment, photocell 222 measures light scattered by the sample. The photocell converts the light received into an electrical signal, which is then transmitted via line 223 to a computer controller 230, which receives the signal as a data input. The computer controller 230 also controls movement of the samples via signal line 231 so that the samples can be sequentially moved into a position between the light source 221 and the photocell 222 upon computer command.

The samples are maintained at a predetermined temperature for a predetermined time to test for storage stability as measured, for example, by the formation of sediment. The predetermined temperature can typically range from about 20° C. to about 80° C., the heat being provided by, for example, an oven in which the samples are stored or passed through. The higher temperature tends to increase the rate of instability. The predetermined humidity will ordinarily range from about 10% relative humidity to 100% relative humidity. The predetermined time is preferably at least about one day. Typically, the samples are tested every day over a period of thirty days. Longer testing times can be selected if desired, e.g., 60 days, 90 days, 365 days, etc.

In general, the samples are initially clear and transparent. Although they can be of any color ranging from, for example, light amber to dark brown, the samples initially allow for the transmission of light therethrough. Sedimentation tends to form a haze or floc, which increases the opacity or light scattering of the sample. Accordingly, a means for measuring the storage stabilty includes determining how much light can pass through or be scattered by the sample. In the system illustrated in FIG. 2, a light source 221 and photocell 222 are employed in a testing station 220 to accomplish this test procedure. The sample is moved into a position in testing station 220 between the light source 221 and the photocell 222, and the photocell measures how much light is transmitted through or be scattered by the sample, converts this measurement into an electrical signal, and transmits the electrical signal through line 223 to a computer controller 230. The computer controller records the signal as data which is stored and included as part of a data library, as described hereinbelow. Alternatively, the computer can convert the transmittance measurement to a Saybolt color or ASTM color value using known software to determine the storage stability of the sample, e.g., by comparing the color value to a known color range of the sample.

The computer controller preferably can also control the movement and positioning of the samples so that they can be individually tested. The test receptacles 212, for example, can be mounted to a movable carriage 211, which moves the test receptacles sequentially into a position between the light source 221 and photocell 222, as shown in FIG. 2. Alternatively, the light source 221 and photocell 222 can be moved. As yet another alternative, the samples can be grasped and individually moved by a robotic arm, as described hereinbelow.

To obtain a base line reading for comparison, the samples are initially tested for storage stability, such as by sedimentation or color measurements, prior to the step of maintaining the samples at a predetermined temperature and optionally a predetermined humidity for a predetermined time. This initial data is stored in the computer library to establish a reference point from which the subsequent storage stability data can be assessed. Preferably, just prior to taking the storage stability measurement the sample is agitated by, for example, vibrating the test receptacle, inverting the test receptacle one or more times, stirring the contents of the test receptacle, or any other suitable means in order to at least temporarily re-suspend any sediment which may have fallen to the bottom of the test receptacle. This step achieves a more uniform distribution of sediment throughout the sample, and therefore a more uniform opacity, so that the photocell does not give a false reading.

Figure 3:
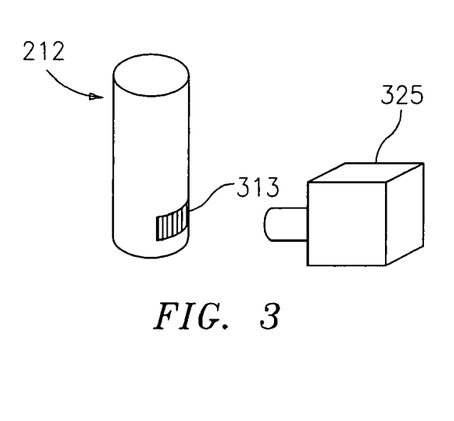
FIG. 3 illustrates a test receptacle having a bar code in conjunction with a bar code reader; and, FIG. 4 is a schematic diagram of a system using a robotic assembly for individually retrieving test receptacles.

Referring now to FIG. 3, optionally, a bar code 313 can be assigned to each individual test receptacle 212 and the sample contained therein. The bar code 313 can be read by a standard bar code reader 325 at each measurement to insure that the data obtained from the sedimentation measurement corresponds to the appropriate sample. This would also facilitate changing the order of the measurement of the samples.

Figure 4:
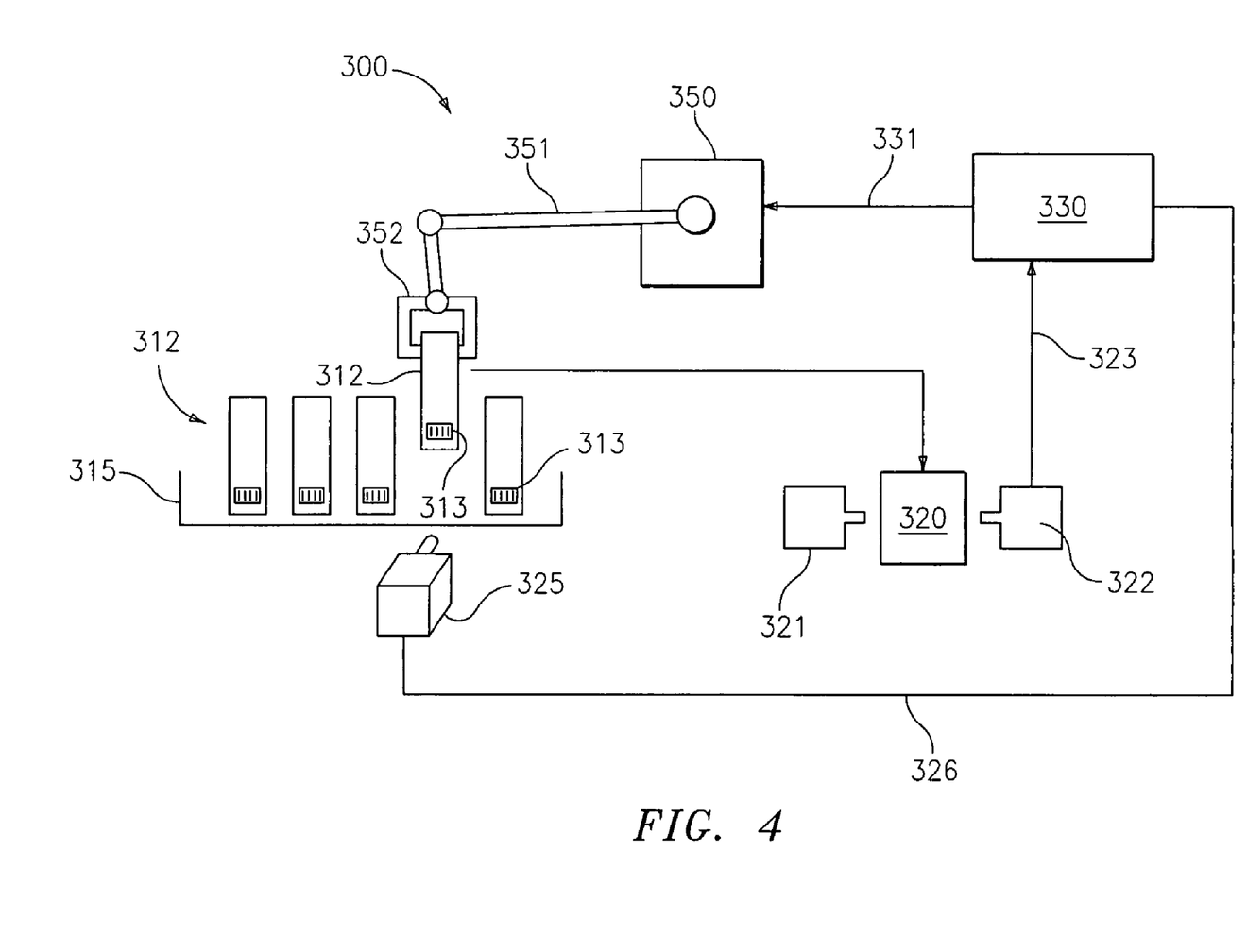

Referring now to FIG. 4, a system 300 is schematically illustrated wherein an array of test receptacles 312 are mounted in a holder 315. Each test receptacle 312 optionally includes an identifying bar code 313 affixed to the outer surface thereof. A bar code reader 325 is positioned so as to be able to read the individual bar codes of the respective test receptacles 312 and to transmit a bar code data signal to a computer controller 330 via a data transmission line 326. The bar code reader 325 is preferably movable with respect to the holder 315 so as to be positionable in alignment with selected individual test receptacles 312.

A robotic assembly 350 includes at least a movable arm 351 with a grasping mechanism 352. The robotic assembly is adapted to grasp an individual test receptacle 312 and move the test receptacle to a position in testing station 320 between the light source 321 and photocell 322 so that it can be measured for sedimentation. The robotic arm is preferably also adapted to agitate the sample in the test receptacle by, for example, by repeatedly inverting the test receptacle 312 before it is placed in position for testing. The photocell obtains a measurement of the light passage through the sample and transmits the light transmission data to the computer controller 330 through a data transmission line 323. The computer controller 330 is operatively associated with controls the robotic assembly via control signal transmission line 331 to selectively retrieve predetermined test receptacles for measurement and then replace them in their assigned respective positions in the holder 315.

In a preferred method, an assigned value of sedimentation is programmed into the computer controller for a "pass/fail" determination. The storage stability measurements are taken daily for a period of extended testing time, for example, 30 days. Those samples which fail during the course of the extended testing time are electronically marked so that they are not retested. By not retesting failed samples the system can be made to operate more efficiently, energy and time being spent only on samples which prospectively meet the desired product specifications.

Alternatively, a viscosity test may be carried out on the plurality of samples to determine storage stability. For example, an impeller (not shown) may be inserted into test receptacles 312 and initially rotated by applying a predetermined power and measuring the revolutions per minute to obtain a base line reading for comparison. Next, at predetermined time intervals the impeller is again rotated by applying the same predetermined power and measuring the revolutions per minute. When the revolutions per minute of the impeller is either higher or lower than the predetermined value of the control sample at a predetermined time, then a "pass/fail" determination can be inputted into the database.

If desired the results of the method of the present invention can be monitored from a remote location, i.e., a location which is not in direct or at least in visual contact with the system operating the method of the invention. A remote location can be, for example, a central process control system or room which, as part of the overall system for use herein, monitors and controls the system as well as records the outputs of each of the results of the tests being carried out. In this way, it becomes possible for less interaction with personnel being stationed at the location of the system. Suitable data lines, with which the results of the output, as well as control commands, may be transmitted, are known.

Storage stability data regarding the lubricating oil additive or lubricating oil compositions can be stored in a relational database to provide a combinatorial lubricating oil composition library. Alternatively, the system may be electrically connected to a signal data collector comprising a computer microprocessor for system operation and control to collect the data from the various tests over an extended period of time to compile the combinatorial lubricating oil composition library. The database can be used to find optimum combinations for a desired product stream, and can be particularly useful when the desired product stream varies depending on market factors. When the product requirements change, appropriate combinations can be selected to prepare the desired product.

Relational database software can be used to correlate the identity of the additive(s) and lubricating oil compositions and the analytical storage stability data obtained therefrom. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the methods described herein. However, any software that is able to create a "memory map" of the lubricating oil additive and lubricating oil compositions and correlate that information with the information obtained from the storage stability measurements can be used. This type of software is well known to those of skill in the art.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A system for screening lubricant performance, under program control, comprising:
    a) a supply of a major amount of at least one base oil of lubricating viscosity;
    b) a supply of a minor amount of at least one lubricating oil additive;
    c) a plurality of test receptacles;
    d) means for conducting molecular modeling of the at least one base oil of lubricating viscosity and the at least one lubricating oil additive to provide leading candidates of the at least one base oil of lubricating viscosity and at least one lubricating oil additive for combination to formulate a leading candidate lubricating oil composition for testing;
    e) means for combining selected quantities of the major amount of the at least one leading base oil of lubricating viscosity candidate with selected quantities of the minor amount of the at least one leading lubricating oil additive candidate in the plurality of test receptacles to form a plurality of leading candidate lubricating oil composition samples in the plurality of test receptacles;
    f) receptacle moving means for individually positioning said test receptacles in a testing station for measurement of storage stability in the respective sample;
    g) means for measuring a first storage stability measurement of the lubricating oil composition sample moved to the testing station and for transferring said first storage stability measurement to a computer controller, wherein said computer controller is operatively connected to the means for individually moving the test receptacles, and further wherein the means for measuring the first storage stability measurement is carried out in the absence of heating each lubricating oil composition sample;
    h) means for measuring a second storage stability measurement of the lubricating oil composition sample moved to the testing station and for transferring said second storage stability measurement to the computer controller, and wherein the means for measuring the second storage stability measurement is carried out after each lubricating oil composition sample is heated to a predetermined temperature for a predetermined time; and
    i) means for comparing said second storage stability measurement to said first storage stability measurement of each lubricating oil composition sample to obtain storage stability data for each sample.

2. The system of claim 1, wherein said means for receptacle moving means comprises a movable carriage.

3. The system of claim 1, wherein the receptacle moving means comprises a robotic assembly having a movable arm for grasping and moving a selected individual receptacle.

4. The system of claim 1, wherein the receptacle moving means comprises means for agitating the test receptacles.

5. The system of claim 1, wherein the testing station includes a light source and a photocell aligned with the light source.

6. The system of claim 1, wherein each test receptacle has a bar code affixed to an outer surface thereof.

7. The system of claim 6, further comprising a bar code reader.

8. A system for screening lubricant performance, under program control, comprising:
    a) a supply of a major amount of at least one base oil of lubricating viscosity;
    b) a supply of a minor amount of at least one lubricating oil additive;
    c) a plurality of test receptacles;
    d) means for conducting molecular modeling of the at least one base oil of lubricating viscosity and the at least one lubricating oil additive to provide leading candidates of the at least one base oil of lubricating viscosity and at least one lubricating oil additive for combination to formulate a leading candidate lubricating oil composition for testing;
    e) means for combining selected quantities of the major amount of the at least one leading base oil of lubricating viscosity candidate with selected quantities of the minor amount of the at least one leading lubricating oil additive candidate in the plurality of test receptacles to form a plurality of leading candidate lubricating oil composition samples in the plurality of test receptacles;
    f) receptacle moving means for individually positioning said test receptacles in a testing station for measurement of storage stability in the respective sample;
    g) means for measuring the storage stability in the sample moved to the testing station to obtain storage stability data associated with said sample and for transferring said storage stability data to a computer controller, wherein said computer controller is operatively connected to the means for individually moving the test receptacles.

9. A high throughput method for screening lubricating oil additive composition samples, under program control, comprising
    (a) conducting molecular modeling of at least one lubricating oil additive to provide leading candidates of the at least one lubricating oil additive to formulate a leading candidate lubricating oil additive sample for testing; and
    (b) containing, under program control, a plurality of the leading candidate lubricating oil additive samples, each sample being in a respective one of a plurality of test receptacles;
    (c) maintaining each sample at a predetermined temperature for a predetermined time;
    (d) measuring the storage stability of each sample to provide storage stability data results for each sample; and,
    (e) outputting the results of step (d).

10. The method of claim 9, wherein the at least one lubricating oil additive is selected from the group consisting of antioxidants, anti-wear agents, detergents, rust ihibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

11. The method of claim 10, wherein the step (c) of maintaining each sample at a predetermined temperature for a predetermined time is performed at a temperature of from about 20° C. to about 80° C.

12. The method of claim 11, wherein the predetermined period of time is at least about one day.

13. The method of claim 10, wherein the step of measuring the storage stability of each sample comprises determining the opacity or light scattering of the sample and comparing the determined opacity or light scattering with the opacity or light scattering of a reference sample.

14. The method of claim 13, wherein the opacity of the sample is determined by measuring the intensity of light passed through a sample.

15. The method of claim 10, further comprising the step of agitating each sample before measuring the storage stability of the sample.

16. The method of claim 9, wherein the plurality of samples are in a linear array and are sequentially moved to a measuring station between a light source and a photocell for individually measuring the storage stability of each sample.

17. The method of claim 9, wherein each sample has affixed thereto a bar code identifying the sample.

18. The method of claim 17, wherein a robotic assembly selectively retrieves individual test receptacles from an array of test receptacles and individually positions said test receptacles in a testing station for determination of the storage stability.

19. The method of claim 18, wherein said robotic assembly is controlled by a computer.

20. The method of claim 19, wherein the result of step (d) for each sample is transmitted to the computer, the computer compares the result with a predetermined value delimiting a failure or passing of the result, and the computer identifies failed samples to preclude further testing of the failed samples.

21. The method of claim 9, wherein the step of outputting comprises storing the result of step (d) on a data carrier.

22. The method of claim 9, further comprising the step of transmitting the result of step (d) to a data carrier at a remote location.

23. The method of claim 9, wherein the storage stability measurement of step (d) comprises a sedimentation measurement, color measurement or a viscosity measurement.

24. The method of claim 9, wherein the plurality of different lubricating oil additive composition samples further comprise a diluent oil to form an additive concentrate.

25. The method of claim 9, wherein the step of molecular modeling is carried out using a computer molecular modeling program.

26. A high throughput method for screening lubricating oil composition samples, under program control, comprising:
(a) conducting molecular modeling of at least one base oil of lubricating viscosity and at least one lubricating oil additive to provide leading candidates of the at least one base oil of lubricating viscosity and at least one lubricating oil additive for combination to formulate a leading candidate lubricating oil composition for testing;
(b) containing, under program control, a plurality of the leading candidate lubricating oil composition samples comprising (i) a major amount of the at least one leading base oil of lubricating viscosity candidate, and (ii) a minor amount of the at least one leading lubricating oil additive candidate in varying percentages in a plurality of test receptacles;
(c) maintaining each sample at a predetermined temperature for a predetermined time;
(d) measuring the storage stability of each sample to provide storage stability data results for each sample; and,
(e) outputting the results of step (d).

27. The method of claim 26, wherein the base oil is a natural or synthetic oil.

28. The method of claim 26, wherein the lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

29. The method of claim 26, wherein the test receptacles are fabricated from a transparent glass.

30. The method of claim 26, wherein the step (c) of maintaining each sample at a predetermined temperature for a predetermined time is performed at a temperature of from about 20° C. to about 80° C.

31. The method of claim 30, wherein the predetermined period of time is at least about one day.

32. The method of claim 30, wherein the step of measuring the storage stability of each sample comprises determining the opacity or light scattering of the sample and comparing the determined opacity or light scattering with the opacity or light scattering of a reference sample.

33. The method of claim 32, wherein the opacity of the sample is determined by measuring the intensity of light passed through a sample.

34. The method of claim 26, further comprising the step of agitating each sample before measuring the storage stability of the sample.

35. The method of claim 26, wherein the plurality of samples are in a linear array and are sequentially moved to a measuring station between a light source and a photocell for individually measuring the storage stability of each sample.

36. The method of claim 26, wherein each sample has affixed thereto a bar code identifying the sample.

37. The method of claim 36, wherein a robotic assembly selectively retrieves individual test receptacles from an array of test receptacles and individually positions said test receptacles in a testing station for determination of storage stability.

38. The method of claim 37, wherein said robotic assembly is controlled by a computer.

39. The method of claim 38, wherein the result of step (d) for each sample is transmitted to the computer, the computer compares the result with a predetermined value delimiting a failure or passing of the result, and the computer identifies failed samples to preclude further testing of the failed samples.

40. The method of claim 26, wherein the step of outputting comprises storing the result of step (d) on a data carrier.

41. The method of claim 26, wherein the storage stability measurement of step (d) comprises a sedimentation measurement, color measurement or a viscosity measurement.

42. The method of claim 26, wherein the step of molecular modeling is carried out using a computer molecular modeling program.

* * * * *